US005843716A

United States Patent [19]
Au-Young et al.

[11] Patent Number: 5,843,716
[45] Date of Patent: Dec. 1, 1998

[54] POLYNUCLEOTIDE ENCODING A PROLINE-RICH MEMBRANE PROTEIN

[75] Inventors: Janice Au-Young, Berkeley; Roger Coleman, Mountain View, both of Calif.

[73] Assignee: Incyte Pharmaceuticals, Inc., Palo Alto, Calif.

[21] Appl. No.: 794,216

[22] Filed: Jan. 30, 1997

[51] Int. Cl.[6] .......................... C12P 21/02; C12N 15/63; C12N 5/10; C07H 21/04
[52] U.S. Cl. ..................... 435/69.1; 435/320.1; 435/325; 435/348; 536/23.5
[58] Field of Search ................................. 536/23.1, 23.5; 435/69.1, 320.1, 325, 348

[56] References Cited

PUBLICATIONS

Hultman, M., et al., "The WashU–Merck EST project –yg96f12.r1 Homo sapiens cDNA clone 41252 5'," *EMBL Database Entry HS158126*, Accession No. R59158, XP002063649, May 29, 1995.

Hillier, L., et al., "The WashU–Merk EST Project.zx41h09.r1 Soares senescent fibroblasts NbHSF Homo sapiens cDNA clone 324929 5'," *EMBL Database Entry HS756342*, Accession No. W48756, XP002063650, May 30, 1996.

Hultman, M. et al., "The WashU–Merck EST project, yw64c10.r1 Homo sapiens cDNA clone 257010 5'," *EMBL Database Entry HS756276*, Accession No. N39756, XP002063651, Jan. 26, 1996.

Rudinger, J. in Peptide Hormones, Parsons (Ed.), University Park Press, Baltimore, MD, pp. 1–7, Jun. 1976.

Hillier, L. et al. The WashU–Merck EST Project, Mar. 1995.

Pinola, M. et al., "Adhesion molecules involved in the interaction of LGL/NK cells and human endothelial cells stimulated with Salmonella bacteria." *Scand. J. Immunol.* (1992) 36:671–679.

Geiger, B. et al., "Cadherins" *Annu.Rev.Cell. Biol.* (1992) 8:307–332.

Field, J.K. "Oncogenes and tumour–suppressor genes in squamous cell carcinoma of the head and neck." *Eur.J.Cancer B. Oral Oncol.* (1992) 28B:67–76.

Tsukita, S. et al., "Specific proto–oncogenic tyrosine kinases of src family are enriched in cell–to–cell adherens junctions where the level of tyrosine phosphorlylation is elevated." *J. Cell Biol.* (1991) 113:867–879.

Volberg, T. et al., "Modulation of intercellurlar adherens–type junctions and tyrosine phosphorylation of their components in RSV–transformed cultured chick lens cells." *Cell Regul.* (1991) 2:105–120.

Hamaguchi, M. et al., "p60v–src causes tyrosine phosphorylation and inactivation of the N–cadherin–catenin cell adhesion system." *EMBO J.* (1993) 12:307–314.

Pawson, T. "Protein modules and signalling networks." *Nature* (1995) 373:573–580.

Feng, S. et al., "Two binding orientations for peptides to the Src SH3 domain; development of a general model for SH3–ligand interactions." *Science* (1994) 266:1241–1247.

Lim, W.A. et al., "Structural determinants of peptide–binding orientation and of sequence specificity in SH3 domains." *Nature* (1994) 372:375–379.

Bunnell, S.C. et al., "Identification of Itk/Tsk Src Homology 3 Domain Ligands." *J.Biol.Chem.* (1996) 271(41):25646–25656.

Pawson, et al., "SH2 and SH3 domains: from structure to function." *Cell* (1992) 71:359–362.

Yang, W. et al., "An SH3–binding Site Conserved in Brutons Tyrosine Kinase and Related Tyrosine Kinases Mediates Specific Protein Interactions in Vitro and in Vivo." *J.Biol. Chem.* (1995) 270(35):20832–28040.

Holmes, T.C. et al., "Association of Src Tyrosine Kinase with a Human Potassium Channel Mediated by SH3 Domain." *Science* (1996) 274:2089–2091.

Kumar, K.N. et al., "Cloning of cDNA for the glutamate–binding subunit of an NMDA receptor complex." *Nature* (1991) 354:70–73. (GI 238267).

Nakanishi, S., "Molecular Diversity of Glutamate Receptors and Implications for Brain Function." *Science* (1992) 258:597–603.

Woods, D.F. et al., "Apical junctions and cell signalling in epithelia." *J.Cell Science* (1993) 17:171–181.

Ridley, A.J. et al., "The small GTP–binding protein rho regulates the assembly of focal adhesions and actin stress fibers in response to growth factors." *Cell* (1992) 70:389–399.

McPhail, L.C. "SH3–dependent assembly of the phagocyte NADPH oxidase." *J.Exp.Med.* (1994) 180:2011–2015.

Kumar, K.N., et al. (GI 238267), GenBank Sequence Database (Accession S61973), National Center for Biotechnology Information, National Library of Medicine, Bethesda, Maryland, 2084, (1991).

Kumar, K.N., et al. (GI 238266) GenBank Sequence Database (Accession S61973), National Center for Biotechnology Information, National Library of Medicine, Bethesda, Maryland, 2084 (1991).

*Primary Examiner*—Frank C. Eisenschenk
*Assistant Examiner*—Evelyn Rabin
*Attorney, Agent, or Firm*—Lucy J. Billings; Incyte Pharmaceuticals, Inc.

[57] ABSTRACT

The present invention provides a human proline-rich membrane protein (PRMP) and polynucleotides which identify and encode PRMP. The invention also provides genetically engineered expression vectors and host cells comprising the nucleic acid sequences encoding PRMP and a method for producing PRMP. The invention also provides for agonists, antibodies, or antagonists specifically binding PRMP, and their use, in the prevention and treatment of diseases associated with expression of PRMP. Additionally, the invention provides for the use of antisense molecules to polynucleotides encoding PRMP for the treatment of diseases associated with the expression of PRMP. The invention also provides diagnostic assays which utilize the polynucleotide, or fragments or the complement thereof, and antibodies specifically binding PRMP.

9 Claims, 9 Drawing Sheets

```
                        9              18             27             36             45             54
5' ATG CCA GCC CCA AAC CTC ATC CCT AGT GGA GGC CTT GCT GAT GTG AAA GTG GCC 63             72             81             90             99            108
   AGG GCC CTC ATG GTA GGC TGG GCA GAA GCC CAA GAA CAG GCT CTA AAG CTG CTA 117            126            135            144            153            162
   AAC CCG GCA GTC CTG GTC CCC GGA GGC TCT TGC CAG TCT GAC AGT GTT CTT GGC 171            180            189            198            207            216
   ACT GCT CAA AGG TCC CAG CAG CTG GGG TTC CCC GTC AGC CCG TGA GCG GCC ATG
                                                                         M 225            234            243            252            261            270
   TCC AAC CCC AGC GCC CCA CCA CCA TAT GAA GAC CGC AAC CCC CTG TAC CCA GGC
   S   N   P   S   A   P   P   P   Y   E   D   R   N   P   L   Y   P   G 279            288            297            306            315            324
   CCT CCG CCC CCT GGG GGC TAT GGG CAG CCA TCT GTC CTG CCA GGA GGG TAT CCT
   P   P   P   P   G   G   Y   G   Q   P   S   V   L   P   G   G   Y   P 333            342            351            360            369            378
   GCC TAC CCT GGC TAC CCG CAG CCT GGC TAC GGT CAC CCT GCT GGC TAC CCA CAG
   A   Y   P   G   Y   P   Q   P   G   Y   G   H   P   A   G   Y   P   Q 387            396            405            414            423            432
   CCC ATG CCC CCC ACC CAC CCG ATG CCC ATG AAC TAC GGC CCA GGC CAT GGC TAT
   P   M   P   P   T   H   P   M   P   M   N   Y   G   P   G   H   G   Y 441            450            459            468            477            486
   GAT GGG GAG GAG AGA GCG GTG AGT GAT AGC TTC GGG CCT GGA GAG TGG GAT GAC
   D   G   E   E   R   A   V   S   D   S   F   G   P   G   E   W   D   D 495            504            513            522            531            540
   CGG AAA GTG CGA CAC ACT TTT ATC CGA AAG GTT TAC TCC ATC ATC TCC GTG CAG
   R   K   V   R   H   T   F   I   R   K   V   Y   S   I   I   S   V   Q 549            558            567            576            585            594
   CTG CTC ATC ACT GTG GCC ATC ATT GCT ATC TTC ACC TTT GTG GAA CCT GTC AGC
   L   L   I   T   V   A   I   I   A   I   F   T   F   V   E   P   V   S 603            612            621            630            639            648
   GCC TTT GTG AGG AGA AAT GTG GCT GTC TAC TAC GTG TCC TAT GCT GTC TTC GTT
   A   F   V   R   R   N   V   A   V   Y   Y   V   S   Y   A   V   F   V 657            666            675            684            693            702
   GTC ACC TAC CTG ATC CTT GCC TGC TGC CAG GGA CCC AGA CGC CGT TTC CCA TGG
   V   T   Y   L   I   L   A   C   C   Q   G   P   R   R   R   F   P   W 711            720            729            738            747            756
   AAC ATC ATT CTG CTG ACC CTT TTT ACT TTT GCC ATG GGC TTC ATG ACG GGC ACC
   N   I   I   L   L   T   L   F   T   F   A   M   G   F   M   T   G   T
```

FIGURE 1A

```
           765         774         783         792         801         810
ATT TCC AGT ATG TAC CAA ACC AAA GCC GTC ATC ATT GCA ATG ATC ATC ACT GCG
 I   S   S   M   Y   Q   T   K   A   V   I   I   A   M   I   I   T   A 819         828         837         846         855         864
GTG GTA TCC ATT TCA GTC ACC ATC TTC TGC TTT CAG ACC AAG GTG GAC TTC ACC
 V   V   S   I   S   V   T   I   F   C   F   Q   T   K   V   D   F   T 873         882         891         900         909         918
TCG TGC ACA GGC CTC TTC TGT GTC CTG GGA ATT GTG CTC CTG GTG ACT GGG ATT
 S   C   T   G   L   F   C   V   L   G   I   V   L   L   V   T   G   I 927         936         945         954         963         972
GTC ACT AGC ATT GTG CTC TAC TTC CAA TAC GTT TAC TGG CTC CAC ATG CTC TAT
 V   T   S   I   V   L   Y   F   Q   Y   V   Y   W   L   H   M   L   Y 981         990         999        1008        1017        1026
GCT GCT CTG GGG GCC ATT TGT TTC ACC CTG TTC CTG GCT TAC GAC ACA CAG CTG
 A   A   L   G   A   I   C   F   T   L   F   L   A   Y   D   T   Q   L 1035        1044        1053        1062        1071        1080
GTC CTG GGG AAC CGG AAG CAC ACC ATC AGC CCC GAG GAC TAC ATC ACT GGC GCC
 V   L   G   N   R   K   H   T   I   S   P   E   D   Y   I   T   G   A 1089        1098        1107        1116        1125        1134
CTG CAG ATT TAC ACA GAC ATC ATC TAC ATC TTC ACC TTT GTG CTG CAG CTG ATG
 L   Q   I   Y   T   D   I   I   Y   I   F   T   F   V   L   Q   L   M 1143        1152        1161        1170        1179        1188
GGG GAT CGC AAT TAA GGA GCA AGC CCC CAT TTT CAC CCG ATC CTG GGC TCT CCC
 G   D   R   N 1197        1206        1215        1224        1233        1242
TTC CAA GCT AGA GGG CTG GGC CCT ATG ACT GTG GTC TGG GCT TTA GGC CCC TTT 1251        1260        1269        1278        1287        1296
CCT TCC CCT TGA GTA ACA TGC CCA GTT TCC TTT CTG TCC TGG AGA CAG GTG GCC 1305        1314        1323        1332        1341        1350
TCT CTG GCT ATG GAT GTG TGG GTA CTT GGT GGG GAC GGA GGA GCT AGG GAC TAA 1359        1368        1377        1386        1395        1404
CTG TTG CTC TTG GTG GGC TTG GCA GGG ACT AGG CTG AAG ATG TGT CTT CTC CCC 1413        1422        1431        1440        1449        1458
GCC ACC TAC TGT ATG ACA CCA CAT TCT TCC TAA CAG CTG GGG TTG TGA GGA ATA 1467        1476        1485        1494        1503        1512
TGA AAA GAG CCT ATT CGA TAG CTA GAA GGG AAT ATG AAA GGT AGA AGT GAC TTC
```

FIGURE 1B

```
            1521          1530          1539          1548          1557          1566
AAG GTC ACG AGG TTC CCC TCC CAC CTC TGT CAC AGG CTT CTT GAC TAC GTA GTT 1575          1584          1593          1602          1611          1620
GGA GCT ATT TCT TCC CCC AGC AAA GCC AGA GAG CTT TGT CCC CGG CCT CCT GGA 1629          1638          1647          1656          1665          1674
CAC ATA GGC CAT TAT CCT GTA TTC CTT TGG CTT GGC ATC TTT TAG CTC AGG AAG 1683          1692          1701          1710          1719          1728
GTA GAA GAG ATC TGT GCC CAT GGG TCT CCT TGC TTC AAT CCC TTC TTG TTT CAG 1737          1746          1755          1764          1773          1782
TGA CAT ATG TAT TGT TTA TCT GGG TTA GGG ATG GGG GAC AGA TAA TAG AAC GAG 1791          1800          1809          1818          1827          1836
CAA AGT AAC CTA TAC AGG CCA GCA TGG AAC AGC ATC TCC CCT GGG CTT GCT CCT 1845          1854          1863          1872          1881          1890
GGC TTG TGA CGC TAT AAG ACA GAG CAG GCC ACA TGT GGC CAT CTG CTC CCC ATT 1899          1908          1917          1926          1935          1944
CTT GAA AGC TGC TGG GGC CTC CTT GCA GGC TTC TGG ATC TCT GGT CAG AGT GAA 1953          1962          1971          1980          1989          1998
CTC TTG CTT CCT GTA TTC AGG CAG CTC AGA GCA GAA AGT AAG GGG CAG AGT CAT 2007          2016          2025          2034          2043          2052
ACG TGT GGC CAG GAA GTA GCC AGG GTG AAG AGA GAC TCG GTG CGG GCA GGG AGA 2061          2070          2079          2088          2097          2106
ATG CCT GGG GGT CCC TCA CCT GGC TAG GGA GAT ACC GAA GCC TAC TGT GGT ACT 2115          2124          2133          2142          2151          2160
GAA GAC TTC TGG GTT CTT TCC TTC TGC TAA CCC AGG GAG GGT CCT AAG AGG AAG 2169          2178          2187          2196          2205          2214
GTG ACT TCT CTC TGT TTG TCT TAA GTT GCA CTG GGG GAT TTC TGA CTT GAG GCC 2223          2232          2241          2250          2259          2268
CAT CTC TCC AGC CAG CCA CTG CCT TCT TTG TAA TAT TAA GTG CCT TGA GCT GGA
```

FIGURE 1C

```
         2277        2286        2295        2304        2313        2322
ATG GGG AAG GGG GAC AAG GGT CAG TCT GTC GGG TGG GGG CAG AAA TCA AAT CAG 2331        2340        2349        2358        2367        2376
CCC AAG GAT ATA GTT AGG ATT AAT TAC TTA ATA GAG AAA TCC TAA CTA TAT CAC 2385        2394        2403        2412        2421        2430
ACA AAG GGA TAC AAC TAT AAA TGT AAT AAA ATT TAT GTC TAG AAG TTA AAA AAA

AAA AAA A 3'
```

```
311  PRVCTLQILNVRTLSATAWKPLSLLPLPRGDRAAFLCHLL  155397
388                                            GI 238267
311  STHCCMSPVCQPIPGSGINTRSQGRRIIPRGEGARLPSCP  155397
428                                            GI 238267
311  SSPGIESPCPLLTLPSEGLAGWGLVLVLGPETKRGWHVSG  155397
468                                            GI 238267
311  ERLSCVLPL                                  155397
508                                            GI 238267
```

FIGURE 2B

| Library | Lib Description | Abun | Pct Abun |
|---|---|---|---|
| HUVELPB01 | HUVEC endothelial cell line, treated cytokine, LPS | 6 | 0.3280 |
| COLNNOM01 | T84 colon epithelial cell line, WM | 1 | 0.1247 |
| PROSTUT12 | prostate tumor, 65 M, match to PROSNOT20 | 4 | 0.1118 |
| PLACNOM03 | placenta, fetal, NORM, WM | 3 | 0.1088 |
| BRAINOM03 | brain, 55 M, NORM, WM | 3 | 0.0809 |
| COLNNOT16 | colon, sigmoid, 62 M, match to COLNTUT03 | 3 | 0.0624 |
| BRAITUT07 | brain tumor, left frontal, 32 M | 2 | 0.0517 |
| SYNORAT03 | synovium, wrist, rheumatoid, 56 F | 3 | 0.0509 |
| BRSTNOT07 | breast, 43 F | 3 | 0.0439 |
| PROSNOT02 | prostate, 50 M, match to PROSTUT01 | 1 | 0.0435 |
| BEPINOT01 | bronchial epithelium, primary cell line, 54 M | 3 | 0.0433 |
| THP1PLB02 | THP-1 promonocyte cell line, treated PMA, LPS | 1 | 0.0407 |
| KERANOT02 | keratinocytes, primary cell line, 30 F | 2 | 0.0364 |
| SPLNFET01 | spleen, fetal | 1 | 0.0352 |
| PROSNOT07 | prostate, 69 M, match to PROSTUT05 | 2 | 0.0336 |
| LIVSFEM02 | liver/spleen, fetal M, NORM, WM | 12 | 0.0316 |
| COLNNOT13 | colon, ascending, 28 M | 1 | 0.0311 |
| STOMNOT02 | stomach, 52 M, match to STOMTUT01 | 1 | 0.0308 |
| BLADTUT02 | bladder tumor, 80 F, match to BLADNOT03 | 1 | 0.0305 |
| BRAINOT12 | brain, right frontal, epilepsy, 5 M | 1 | 0.0303 |
| COLNNOT27 | large intestine, cecum, Crohn's, 31 M | 1 | 0.0303 |
| COLNNOT05 | colon, 40 M, match to COLNCRT01 | 1 | 0.0289 |
| FIBRSEM01 | fibroblasts, senescent, NORM, WM | 1 | 0.0289 |
| SYNORAT05 | synovium, knee, rheumatoid, 62 F | 1 | 0.0286 |
| SININOT01 | small intestine, ileum, 4 F | 1 | 0.0280 |
| BRSTTUT02 | breast tumor, 54 F, match to BRSTNOT03 | 2 | 0.0279 |
| PLACNOM02 | placenta, neonatal F, NORM, WM | 5 | 0.0278 |
| THYRNOT03 | thyroid tumor, adenoma, 28 F | 2 | 0.0277 |
| THYRTUT03 | thyroid tumor, benign, 17 M | 1 | 0.0276 |
| SINTNOT13 | small intestine, ileum, ulcerative colitis, 25 F | 1 | 0.0275 |
| CONNTUT01 | skull tumor, chondroid chordoma, 30 F | 1 | 0.0271 |
| PROSNOT26 | prostate, 65 M | 1 | 0.0270 |
| ENDCNOT01 | endothelial cells, coronary artery, 58 M | 1 | 0.0268 |
| LUNGNOM01 | lung, 72 M, WM | 1 | 0.0267 |
| PROSTUT08 | prostate tumor, 60 M, match to PROSNOT14 | 1 | 0.0266 |
| BRSTNOM01 | breast, F, NORM, WM | 1 | 0.0264 |
| LUNGNOT10 | lung, fetal M | 1 | 0.0261 |
| LIVRTUT01 | liver tumor, metastasis, 51 F | 1 | 0.0259 |
| SINTFET03 | small intestine, fetal F | 2 | 0.0259 |
| LUNGNOT14 | lung, 47 M | 1 | 0.0259 |
| BRSTNOT09 | breast, 45 F, match to BRSTTUT08 | 1 | 0.0255 |
| PANCNOT08 | pancreas, 65 F, match to PANCTUT01 | 1 | 0.0254 |
| UTRSNOT02 | uterus, 34 F | 3 | 0.0233 |
| NERVMSM01 | multiple sclerosis, 46 M, NORM, WM | 1 | 0.0224 |
| BRAINOM01 | brain, infant F, NORM, WM | 5 | 0.0223 |
| TMLR2DT01 | lymphocytes (non-adher PBMNC), M/F, 24-hr MLR | 1 | 0.0212 |
| KIDNNOT05 | kidney, neonatal F | 2 | 0.0211 |
| OVARTUT01 | ovarian tumor, 43 F, match to OVARNOT03 | 2 | 0.0207 |
| UTRPNOM01 | uterus, F, NORM, WM | 1 | 0.0201 |
| LUNGNOT03 | lung, 79 M, match to LUNGTUT02 | 1 | 0.0200 |
| SYNORAB01 | synovium, hip, rheumatoid, 68 F | 1 | 0.0195 |
| BRSTNOT04 | breast, 62 F | 2 | 0.0192 |
| MELANOM01 | melanocytes, M, NORM, WM | 2 | 0.0192 |

FIGURE 4A

| | | | |
|---|---|---|---|
| LUNGAST01 | lung, asthma, 17 M | 2 | 0.0189 |
| LUNGTUT02 | lung tumor, metastasis, 79 M, match to LUNGNOT03 | 1 | 0.0189 |
| MMLR2DT01 | macrophages (adher PBMNC), M/F, 48-hr MLR | 1 | 0.0178 |
| PANCNOT04 | pancreas, 5 M | 1 | 0.0169 |
| UCMCL5T01 | mononuclear cells, treated IL-5 | 2 | 0.0168 |
| LUNGTUT03 | lung tumor, 69 M, match to LUNGNOT15 | 1 | 0.0159 |
| NEUTGMT01 | granulocytes, periph blood, M/F, treated GM-CSF | 1 | 0.0156 |
| BRAITUT02 | brain tumor, metastasis, 58 M | 2 | 0.0149 |
| BRSTNOT05 | breast, 58 F, match to BRSTTUT03 | 2 | 0.0149 |
| COLNNOT11 | colon, 60 M | 1 | 0.0149 |
| CONNNOT01 | fat, mesentery, 71 M | 1 | 0.0149 |
| BRAITUT03 | brain tumor, astrocytoma, 17 F | 2 | 0.0148 |
| BRSTNOT03 | breast, 54 F, match to BRSTTUT02 | 1 | 0.0147 |
| NGANNOT01 | ganglioneuroma, 9 M | 2 | 0.0146 |
| PROSTUT05 | prostate tumor, 69 M, match to PROSNOT07 | 1 | 0.0145 |
| LATRTUT02 | heart tumor, myoma, 43 M | 1 | 0.0137 |
| PITUNOT02 | pituitary, 15-75 M/F | 1 | 0.0135 |
| TESTTUT02 | testicular tumor, 31 M | 1 | 0.0134 |
| PROSNOT16 | prostate, 68 M | 1 | 0.0132 |
| OVARNOT02 | ovary, 59 F | 1 | 0.0112 |
| BRSTTUT01 | breast tumor, 55 F, match to BRSTNOT02 | 1 | 0.0095 |
| PROSNON01 | prostate, 28 M, NORM | 1 | 0.0094 |
| CARDFEM01 | heart, fetal, NORM, WM | 1 | 0.0083 |
| LUNGFET03 | lung, fetal F | 1 | 0.0069 |

FIGURE 4B

POLYNUCLEOTIDE ENCODING A PROLINE-RICH MEMBRANE PROTEIN

FIELD OF THE INVENTION

This invention relates to nucleic acid and amino acid sequences of a novel proline-rich membrane protein and to the use of these sequences in the diagnosis, prevention, and treatment of autoimmune and inflammatory diseases and disorders relating to abnormal cellular proliferation, including atherosclerosis and cancer.

BACKGROUND OF THE INVENTION

For the maintenance of an efficient immune defense system, lymphocytes actively migrate between the various lymphoid and non-lymphoid tissues of the body by way of the bloodstream in order to detect sites of antigen exposure. This migration involves movement through intact vascular endothelium and requires interactions between receptors on lymphocytes and ligands displayed by vascular endothelial cells. Exposure to various pro-inflammatory mediators, such as cytokines, lipopolysaccharide endotoxin (LPS), and tumor necrosis factor (TNF), increases the adhesion of lymphocytes to human umbilical vein endothelial cells (HUVECs) by up-regulating the expression of intracellular adhesion molecules and vascular cell adhesion molecules (ICAMs and VCAMs; Pinola, M. et al. (1992) Scand. J. Immunol. 36:671–679). This up-regulation represents an activation state which provides characteristic anchorage sites for the increased migration of lymphocytes towards the site of inflammation.

In the presence of various pro-inflammatory mediators, endothelial cell-derived adhesion molecules initiate the adherence of lymphocytes to endothelium and thus begin the early phases of immunologically mediated inflammation. Upon exposure to mediators present at inflamed or infected sites, lymphocytes react with increased chemotaxis and adherence to endothelium, leading to degranulation, oxidative metabolism, and pathogen killing. Although critical for effective host defense, these events are also in part responsible for tissue damage associated with inflammation. Abnormalities in lymphocyte trafficking and inflammatory responses are causative factors in inflammatory and autoimmune diseases.

Adhesion molecules also mediate cell-cell interactions which control the fate and proliferation of epithelial cells. Interactions between epithelial cells, in the form of specialized junctions, control cell proliferation, differentiation, and morphogenesis. Apical junctions such as adherens junctions are associated with actin microfilaments, and at least one group of cell adhesion molecules, the cadherins. The cadherins and their associated anchoring molecules, the catenins, have been localized at adherens junctions (Geiger, B. et al. (1992) Ann. Rev. Cell Biol. 8:307–332). Loss of expression of cadherins and related molecules is associated with loss of cell proliferation control (Field, J. K. (1992) Eur. J. Cancer (B) 28B:67–76).

Adherens junctions also participate in cell-cell interactions through their association with a protein tyrosine kinase (PTK)-mediated signaling pathway. Tyrosine phosphorylation at adherens junctions is partly a function of non-receptor PTKs. Two such kinases, c-Yes and c-Src, are highly enriched in the adherens junctions of hepatocytes, kidney epithelial cells, and keratinocytes (Tsukita, S. et al. (1991) J. Cell Biol. 113:867–879). Expression of the oncogenic v-Src in epithelial cells causes abnormally high levels of tyrosine phosphorylation, breakdown of adherens junctions and loss of cell-cell adhesion (Volberg, T. et al. (1991) Cell Regul. 2:105–120). The cadherin/catenin complexes are particularly susceptible to oncogenic phosphorylation. Fibroblasts and epithelial cells transformed with v-Src express cadherins which become hyperphosphorylated and are thus unable to function properly in cell adhesion or metastasis suppression (Hamaguchi, M. et al. (1993) EMBO J. 12:307–314).

Many polypeptide hormones, cytokines, antigens, and components of the extracellular matrix bind membrane-spanning receptors which signal through associated cytoplasmic non-receptor receptor PTK domains. Although the targets of these PTKs may have vastly different biochemical activities and biological functions, they often recognize related sequence elements. These sequence elements, known as Src-homology-2 (SH2), Src-homology-3 (SH3), and plecstrin homology (PH) domains, can fold into independent, compact binding modules. SH2 domains bind short phosphotyrosine-containing peptide motifs, SH3 domains bind short peptide motifs which contain one or more proline residues, and PH domains may associate with phospholipids. These conserved protein domains form "binding modules" (Pawson, T. (1995) Nature 373:573–580) which mediate intermolecular protein-protein associations.

The SH3 binding module consists of the complex of a proline-rich peptide domain (PRD) on one protein with an SH3 domain on another protein. The PRD usually consists of seven to ten amino acids and contains the consensus sequence X-P-X-X-P, where X is usually an aliphatic residue. The PRD forms a left-handed polyproline type II helix. Each X-P pair fits into a hydrophobic pocket formed by conserved aromatic residues of the SH3 domain (Feng, S. et al. (1994) Science 266:1241–1246; Lim, W. A. et al. (1994) Nature 372:375–379).

The conserved noncatalytic domains of many non-receptor PTKs are required for intermolecular interactions with activators and effectors, as well as intramolecular regulatory interactions (Bunnell S. C. et al. (1996) J. Biol. Chem. 271:25646–25656; Pawson, T. et al. (1992) Cell 71:359–362). PRDs in several such kinases, such as Btk and Itk, are recognized by the SH3 domains of various Src family kinases. The PRDs in Btk and Itk contain the consensus sequence XPΦPPXP, where Φ denotes a hydrophobic residue (Yang, W. et al. (1995) J. Biol. Chem 270:20832–20840).

Mutations in Btk have been associated with immunodeficiencies in man and mouse. In addition, Btk is found in association with an as yet unidentified 72-kDa phosphotyrosine-containing protein, an interaction that requires a functional PRD in Btk (Yang et al., supra). The SH3-binding PRD of Btk may therefore interact in vivo with proteins that regulate the phosphorylation state of Btk and thus regulate the participation of Btk in various receptor-mediated signaling pathways (Yang et al., supra).

Numerous mammalian ion channels such as the human Kv1.5 potassium channel (hKv1.5) contains PRDs. Direct association of the SH3 domain of Src tyrosine kinase with the PRDs of hKv1.5 was observed (Holmes, T. C. et al. (1996) Science 274:2089–2091). Holmes et. al. propose that closely associated channel-kinase signaling complexes may serve to increase the specificity of signaling pathways.

Subunits of the N-methyl D-aspartate (NMDA) receptor complex contain PRDs which may interact with SH3 domain-containing signaling molecules. The NMDA receptor complex is a postsynaptic cation channel activated by the excitatory neurotransmitter glutamic acid and specific for the agonist NMDA. A putative NMDA receptor glutamate-binding protein which contains PRDs in the N-terminal region has been cloned from rat brain (Kumar, K. N. et al. (1991) Nature 354:70–73). While this protein exhibits the binding characteristics of an NMDA receptor subunit (Kumar, supra), the role of the glutamate-binding protein as an NMDA receptor subunit has been questioned (Nakanishi, S. (1992) Science 258:597–603).

Proteins which contain SH3 domains or SH3-binding PRDs are also important for cellular organization and the control of cellular morphology. Several proteins associated with the cytoskeleton, including α-spectrin and myosin-1, contain SH3 domains (Pawson 1995, supra). Numerous SH3 domain-containing proteins in yeast are required for organization or polarization of the actin cytoskeleton (Pawson 1995, supra).

Mutations in the SH3 domain-containing Drosophila tumor-suppressor gene discs large (dlg) lead to a loss of the tight (septate) junctions between epithelial cells and result in loss of apical-basal polarity and aberrant cell proliferation (Woods, D. F. et al. (1993) J. Cell Sci, Suppl. 17:171–181). Dlg protein is expressed in most epithelial tissues throughout development. Potential ligands for the mammalian homologues of Dlg include the small GTP-binding protein rho. Rho binds with high affinity to SH3 domains, is involved in actin bundling, and regulates the assembly of focal adhesions (Ridley, A. J. et al. (1992) Cell 70:389–399; Woods et al., supra).

In phagocytes, the NADPH oxidase mutiprotein complex is activated by inflammatory stimuli to produce superoxide, a precursor for antimicrobial oxidants. This activation is dependent on the interaction of SH3 domain-containing oxidase proteins p47-phox, p67-phox, and p40-phox with other proteins of the oxidase complex (McPhail, L. C. (1994) J. Exp. Med. 180:2011–2015). The SH3 domains of p47-phox and p67-phox may be responsible for assembly of the finctional oxidase complex (Pawson 1995, supra). For instance, a mutation of proline to glutamine in the PRD of the oxidase component p22-phox was detected in a patient with chronic granulomatous disease, a condition characterized by high susceptibility to bacterial and fungal infections. The mutation blocked the interaction of p22-phox with the p47-phox SH3 domain.

The discovery of polynucleotides encoding a novel proline-rich membrane protein, and the molecules themselves, provides a means to investigate cell signaling, protein trafficking and subcellular localization, the control of cellular architecture, cell-cell interactions, cellular proliferation, and inflammatory and immune responses under normal and disease conditions. Discovery of a novel proline-rich membrane protein satisfies a need in the art by providing new compositions useful in diagnosing and treating autoimmune and inflammatory diseases and disorders relating to abnormal cellular proliferation, including atherosclerosis and cancer.

SUMMARY OF THE INVENTION

The present invention features a novel proline-rich membrane protein hereinafter designated PRMP and characterized as having similarity to rat NMDA receptor glutamic acid binding subunit.

Accordingly, the invention features a substantially purified PRMP having the amino acid sequence shown in SEQ ID NO:1.

One aspect of the invention features isolated and substantially purified polynucleotides that encode PRMP. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode PRMP. The present invention also features antibodies which bind specifically to PRMP, and pharmaceutical compositions comprising substantially purified PRMP. The invention also features the use of agonists and antagonists of PRMP. The invention also features methods for treating disorders which are associated with PRMP, and for detecting a polynucleotide which encodes PRMP.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of PRMP. The alignment was produced using MacDNASIS PRO™ software (Hitachi Software Engineering Co., Ltd., San Bruno, Calif.).

FIGS. 2A and 2B show the amino acid sequence alignments between PRMP (SEQ ID NO:1), rat NMDA receptor glutamate-binding subunit (GI 238267; SEQ ID NO:3). The alignment was produced using the multisequence alignment program of DNASTAR™ software (DNASTAR Inc, Madison Wis.).

FIGS. 4A and 4B show the northern analysis for SEQ ID NO:2. The northern analysis was produced electronically using LIFESEQ™ database (Incyte Pharmaceuticals, Inc., Palo Alto, Calif.).

DESCRIPTION OF THE INVENTION

Figure 3A:
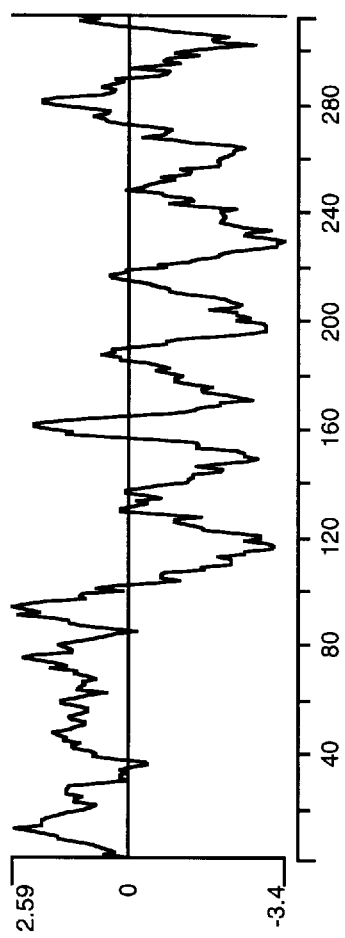
FIGS. 3A and 3B show the hydrophobicity plots (produced using the protein analysis program of DNASTAR software) for PRMP, SEQ ID NO:1; and rat NMDA receptor glutamate-binding subunit, SEQ ID NO:3. The positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence, and fragments or portions thereof, and to naturally occurring or synthetic molecules.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

PRMP, as used herein, refers to the amino acid sequences of substantially purified PRMP obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using an XL-PCR kit (Perkin Elmer, Norwalk, Conn.) in the 5' and/or the 3' direction and resequenced, or which has been assembled from the overlapping sequences of more than one Incyte clone using the GEL VIEW fragment assembly system (GCG, Madison, Wis.), or which has been both extended and assembled.

A "variant" of PRMP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic PRMP, or any oligopeptide thereof, to induce a specific immune response in appropriate animals or cells and to bind with specific antibodies.

The term "agonist", as used herein, refers to a molecule which, when bound to PRMP, causes a change in PRMP which modulates the activity of PRMP. Agonists may include proteins, nucleic acids, carbohydrates, or any other molecules which bind to PRMP.

The terms "antagonist" or "inhibitor", as used herein, refer to a molecule which, when bound to PRMP, blocks or modulates the biological or immunological activity of PRMP. Antagonists and inhibitors may include proteins, nucleic acids, carbohydrates, or any other molecules which bind to PRMP.

The term "modulate", as used herein, refers to a change or an alteration in the biological activity of PRMP. Modulation may be an increase or a decrease in protein activity, a change in binding characteristics, or any other change in the biological, functional or immunological properties of PRMP.

The term "mimetic", as used herein, refers to a molecule, the structure of which is developed from knowledge of the structure of PRMP or portions thereof and, as such, is able to effect some or all of the actions of PRD-containing molecules.

The term "derivative", as used herein, refers to the chemical modification of a nucleic acid encoding PRMP or the encoded PRMP. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm–5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human PRMP and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding PRMP or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 by northern analysis is indicative of the presence of mRNA encoding PRMP in a sample and thereby correlates with expression of the transcript from the polynucleotide encoding the protein.

"Alterations" in the polynucleotide of SEQ ID NO:2, as used herein, comprise any alteration in the sequence of polynucleotides encoding PRMP including deletions, insertions, and point mutations that may be detected using hybridization assays. Included within this definition is the detection of alterations to the genomic DNA sequence which encodes PRMP (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the polynucleotide sequence encoding PRMP (e.g., using fluorescent in situ hybridization (FISH) to metaphase chromosomes spreads).

As used herein, the term "antibody" refers to intact molecules as well as fragments thereof, such as Fab, F(ab')$_2$, and Fv, which are capable of binding the epitopic determinant. Antibodies that bind PRMP polypeptides can be prepared using intact polypeptides or fragments containing small peptides of interest as the immunizing antigen. The polypeptide or peptide used to immunize an animal can be derived from the transition of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of a novel human proline-rich membrane protein (PRMP), the polynucleotides encoding PRMP, and the use of these compositions for the diagnosis, prevention, or treatment of autoimmune and inflammatory diseases and disorders relating to abnormal cellular proliferation including atherosclerosis and cancer.

Nucleic acids encoding the human PRMP of the present invention were first identified in Incyte Clone 155397 from the PMA/LPS-treated promonocyte cell line cDNA library (THP1PLB02) through a computer-generated search for amino acid sequence alignments. A consensus sequence, SEQ ID NO:2, was derived from extension of Incyte Clone 155397 (THP1PLB02).

Figure 2A:
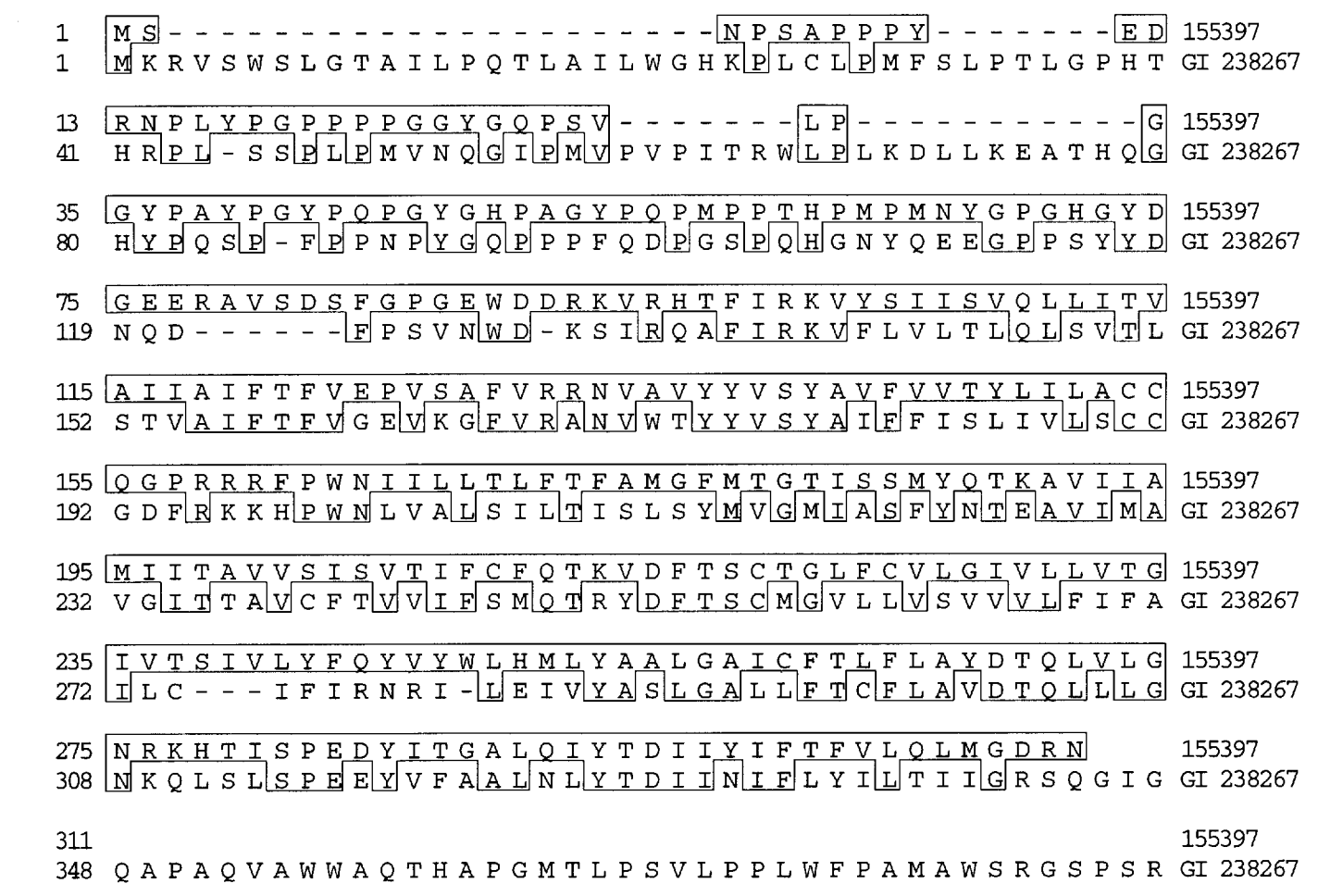
Figure 3B:
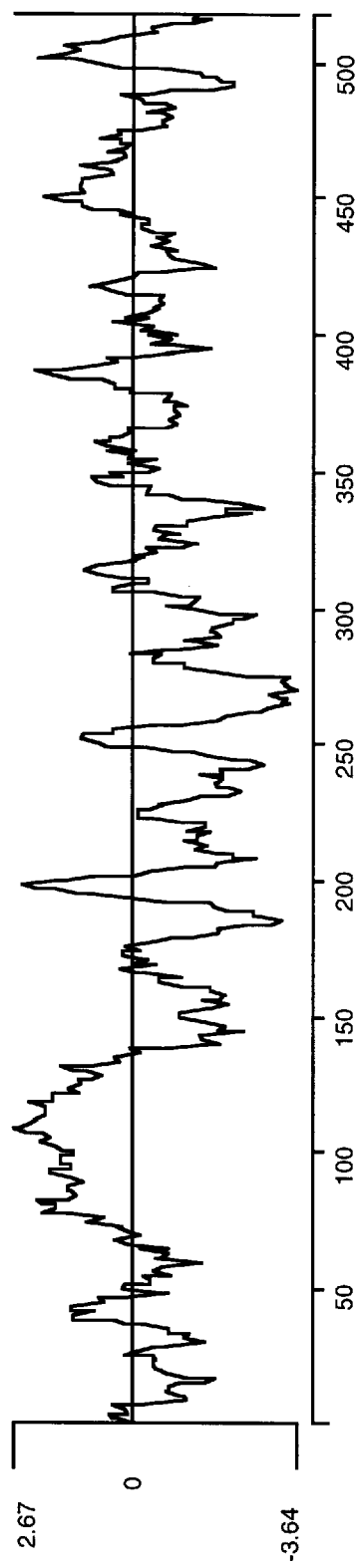

In one embodiment, the invention encompasses a polypeptide comprising the amino acid sequence of SEQ ID NO:1, as shown in FIGS. 1A, 1B, 1C, and 1D PRMP is 311 amino acids in length and has chemical and structural homology with the central portion of rat NMDA receptor glutamate-binding subunit (GI 238267; SEQ ID NO:3). In particular, PRMP shares 41% identity to the central portion of rat NMDA receptor glutamate-binding subunit (FIGS. 2A and 2B). PRMP contains up to seven potential transmembrane domains located approximately at amino acid residues 102–123, 133–152, 163–182, 191–212, 222–243, 251–271, and 288–307 of SEQ ID NO:1. Of particular note is the high proportion of proline and tyrosine residues in the N-terminal sequence of PRMP prior to the first transmembrane domain (25% pro and 10% tyr), which suggests the presence of SH3-binding PRDs and tyrosine phosphorylation sites. As illustrated by FIGS. 3A and 3B, PRMP has a similar hydrophobicity profile to the central portion of rat NMDA receptor glutamate-binding subunit. Northern analysis (FIGS. 4A and 4B) shows the abundant expression of PRMP in the HUVEC endothelial cell line activated by proinflammatory mediators. In addition, PRMP is found in numerous epithelial and endothelial tissues and cell lines; cells and tissues involved in immune response and inflammation; and tumor-associated epithelial tissues.

The invention also encompasses PRMP variants. A preferred PRMP variant is one having at least 80%, and more preferably 90%, amino acid sequence identity to the PRMP amino acid sequence (SEQ ID NO:1). A most preferred PRMP variant is one having at least 95% amino acid sequence identity to SEQ ID NO:1.

The invention also encompasses polynucleotides which encode PRMP. Accordingly, any nucleic acid sequence which encodes the amino acid sequence of PRMP can be used to generate recombinant molecules which express PRMP. In a particular embodiment, the invention encompasses the polynucleotide comprising the nucleic acid sequence of SEQ ID NO:2 as shown in FIGS. 1A, 1B, 1C, and 1D.

It will be appreciated by those skilled in the art that as a result of the degeneracy of the genetic code, a multitude of nucleotide sequences encoding PRMP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring PRMP, and all such variations are to be considered as being specifically disclosed.

Although nucleotide sequences which encode PRMP and its variants are preferably capable of hybridizing to the nucleotide sequence of the naturally occurring PRMP under appropriately selected conditions of stringency, it may be advantageous to produce nucleotide sequences encoding PRMP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding PRMP and its derivatives without altering the encoded amino acid sequences include the production of RNA transcripts having more desirable properties, such as a greater half-life, than transcripts produced from the naturally occurring sequence.

The invention also encompasses production of DNA sequences, or portions thereof, which encode PRMP and its derivatives, entirely by synthetic chemistry. After production, the synthetic sequence may be inserted into any of the many available expression vectors and cell systems using reagents that are well known in the art at the time of the filing of this application. Moreover, synthetic chemistry may be used to introduce mutations into a sequence encoding PRMP or any portion thereof.

Also encompassed by the invention are polynucleotide sequences that are capable of hybridizing to the claimed nucleotide sequences, and in particular, those shown in SEQ ID NO:2, under various conditions of stringency. Hybridization conditions are based on the melting temperature (Tm) of the nucleic acid binding complex or probe, as taught in Wahl, G. M. and S. L. Berger (1987; Methods Enzymol. 152:399–407) and Kimmel, A. R. (1987; Methods Enzymol. 152:507–511), and may be used at a defined stringency.

Altered nucleic acid sequences encoding PRMP which are encompassed by the invention include deletions, insertions, or substitutions of different nucleotides resulting in a polynucleotide that encodes the same or a fluctionally equivalent PRMP. The encoded protein may also contain deletions, insertions, or substitutions of amino acid residues which produce a silent change and result in a functionally equivalent PRMP. Deliberate amino acid substitutions may be made on the basis of similarity in polarity, charge, solubility, hydrophobicity, hydrophilicity, and/or the amphipathic nature of the residues as long as the biological activity of PRMP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the genes encoding PRMP. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE polymerase (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton MICRO LAB 2200 (Hamilton, Reno, Nev.), Peltier Thermal Cycler (PTC200; MJ Research, Watertown, Mass.) and the ABI 377 DNA sequencers (Perkin Elmer).

The nucleic acid sequences encoding PRMP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk in genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode PRMP, or fusion proteins or functional equivalents thereof, may be used in recombinant DNA molecules to direct expression of PRMP in appropriate host cells. Due to the inherent degeneracy of the genetic code, other DNA sequences which encode substantially the same or a functionally equivalent amino acid sequence may be produced and these sequences may be used to clone and express PRMP.

As will be understood by those of skill in the art, it may be advantageous to produce PRMP-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter PRMP encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and so forth.

In another embodiment of the invention, natural, modified, or recombinant nucleic acid sequences encoding PRMP may be ligated to a heterologous sequence to encode a fusion protein. For example, to screen peptide libraries for inhibitors of PRMP activity, it may be useful to encode a chimeric PRMP protein that can be recognized by a commercially available antibody. A fusion protein may also be engineered to contain a cleavage site located between the PRMP encoding sequence and the heterologous protein sequence, so that PRMP may be cleaved and purified away from the heterologous moiety.

In another embodiment, sequences encoding PRMP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of PRMP, or a portion thereof. For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, W H Freeman and Co., New York, N.Y.). The composition of the synthetic peptides may be confirmed by amino acid analysis or sequencing (e.g., the Edman degradation procedure; Creighton, supra). Additionally, the amino acid sequence of PRMP, or any part thereof, may be altered during direct synthesis and/or combined using chemical methods with sequences from other proteins, or any part thereof, to produce a variant polypeptide.

In order to express a biologically active PRMP, the nucleotide sequences encoding PRMP or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding PRMP and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding PRMP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or PSPORT1 plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding PRMP, vectors based on SV40 or EBV may be used with an appropriate selectable marker.

In bacterial systems, a number of expression vectors may be selected depending upon the use intended for PRMP. For example, when large quantities of PRMP are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding PRMP may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding PRMP may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al.

(1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express PRMP. For example, in one such system, *Autographa californica* nuclear polyhedrosis virus (AcNPV) is used as a vector to express foreign genes in *Spodoptera frugiperda* cells or in Trichoplusia larvae. The sequences encoding PRMP may be cloned into a non-essential region of the virus, such as the polyhedrin gene, and placed under control of the polyhedrin promoter. Successful insertion of PRMP will render the polyhedrin gene inactive and produce recombinant virus lacking coat protein. The recombinant viruses may then be used to infect, for example, *S. frugiperda* cells or Trichoplusia larvae in which PRMP may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding PRMP may be ligated into an adenovirus transcription/translation complex consisting of the late promoter and tripartite leader sequence. Insertion in a non-essential E1 or E3 region of the viral genome may be used to obtain a viable virus which is capable of expressing PRMP in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of sequences encoding PRMP. Such signals include the ATG initiation codon and adjacent sequences. In cases where sequences encoding PRMP, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express PRMP may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk$^-$ or aprt$^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding PRMP is inserted within a marker gene sequence, recombinant cells containing sequences encoding PRMP can be identified by the absence of marker gene function. Alternatively, a marker gene can be placed in tandem with a sequence encoding PRMP under the control of a single promoter. Expression of the marker gene in response to induction or selection usually indicates expression of the tandem gene as well.

Alternatively, host cells which contain the nucleic acid sequence encoding PRMP and express PRMP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding PRMP can be detected by DNA-DNA or DNA-RNA hybridization or amplification using probes or portions or fragments of polynucleotides encoding PRMP. Nucleic acid amplification based assays involve the use of oligonucleotides or oligomers based on the sequences encoding PRMP to detect transformants containing DNA or RNA encoding PRMP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of PRMP, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on PRMP is preferred, but a competitive binding assay may be employed. These and other assays are described, among other places, in Hampton, R. et al. (1990; Serological Methods, a Laboratory Manual, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding PRMP include oligolabeling, nick translation, end-labeling or PCR amplification using a labeled nucleotide. Alternatively, the sequences encoding PRMP, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., (Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with nucleotide sequences encoding PRMP may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode PRMP may be designed to contain signal sequences which direct secretion of PRMP through a prokaryotic or eukaryotic cell membrane. Other recombinant constructions may be used to join sequences encoding PRMP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and PRMP may be used to facilitate purification. One such expression vector provides for expression of a fusion protein containing PRMP and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3:263–281) while the enterokinase cleavage site provides a means for purifying PRMP from the fusion protein. A discussion of vectors which contain fusion proteins is provided in Kroll, D. J. et al. (1993; DNA Cell Biol. 12:441–453).

In addition to recombinant production, fragments of PRMP may be produced by direct peptide synthesis using solid-phase techniques (Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of PRMP may be chemically synthesized separately and combined using chemical methods to produce the full length molecule.

THERAPEUTICS

Chemical and structural homology exists between PRMP and NMDA receptor glutamate-binding subunit from rat. In addition, the presence of proline-rich domains, and the expression of PRMP in inflammation-activated endothelial cells, tumor-associated tissues of epithelial origin, and other tissues involved in immune or inflammatory disorders, suggests that PRMP has a role in cell signaling, protein trafficking and subcellular localization, control of cell architecture, cell-cell interactions, cell growth and development, and modulation of immune and inflammatory responses.

Therefore, in one embodiment, PRMP or a fragment or derivative thereof may be administered to a subject or cells removed from a subject to promote tissue or organ regeneration. This embodiment would be of particular benefit in promoting regeneration of endothelial or epithelial tissues.

In another embodiment, a vector capable of expressing PRMP, or a fragment or derivative thereof, may also be administered to a subject or cells isolated from a subject to promote tissue or organ regeneration.

In another embodiment, a vector expressing antisense of the polynucleotide encoding PRMP may be administered to a subject to treat or prevent a disorder which is associated with expression of PRMP. Such disorders may include, but are not limited to, inflammatory and allergic conditions such as rheumatoid and osteoarthritis, asthma, allergic rhinitis, atopic dermatitis; autoimmune conditions such as Sjögren's syndrome, scleroderma, hyperthyroidism (Grave's disease), systemic lupus, myasthenia gravis, autoimmune thyroiditis, diabetes mellitus, pancreatitis, ulcerative colitis, Crohn's disease, atrophic gastritis, and graft-vs-host disease; disorders relating to abnormal cellular differentiation, proliferation, or degeneration, including arteriosclerosis, atherosclerosis, hyperaldosteronism, hypocortisolism (Addison's disease), hypothyroidism, colorectal polyps, gastric and duodenal ulcers, cancers of hematopoietic cells and lymphoid tissues including leukemias, lymphomas (including Hodgkin's disease), lymphosarcomas and myelomas, and carcinomas of glands, tissues, and organs involved in secretion or absorption, including prostate, pancreas, lung, tongue, brain, breast, and bladder, adrenal gland, thyroid, liver, uterus, kidney, testes, and organs of the gastrointestinal tract including small intestine, colon, rectum, and stomach.

In another embodiment, antagonists or inhibitors of PRMP may be administered to a subject to treat or prevent any of the disorders associated with expression of PRMP including those listed above. In a particular aspect, antibodies which are specific for PRMP may be used directly as an antagonist, or indirectly as a targeting or delivery mechanism for bringing a pharmaceutical agent to cells or tissue which express PRMP.

In other embodiments, any of the therapeutic proteins, antagonists, antibodies, agonists, antisense sequences or vectors described above may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of PRMP may be produced using methods which are generally known in the art. In particular, purified PRMP may be used to produce antibodies or to screen libraries of pharmaceutical agents to identify those which specifically bind PRMP.

Antibodies specific for PRMP may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with PRMP or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to PRMP have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of PRMP amino acids may be fused with those of another protein such as keyhole limpet hemocyanin and antibody produced against the chimeric molecule.

Monoclonal antibodies to PRMP may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity, can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce PRMP-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, R. et al. (1989) Proc. Natl. Acad. Sci. 86:3833–3837; Winter, G. et al. (1991) Nature 349:293–299).

Antibody fragments which contain specific binding sites for PRMP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between PRMP and its specific antibody. A two-site, monoclonal-based immunoassay utilizing monoclonal antibodies reactive to two non-interfering PRMP epitopes is preferred, but a competitive binding assay may also be employed (Maddox, supra).

In another embodiment of the invention, the polynucleotides encoding PRMP, or any fragment thereof, or antisense molecules, may be used for therapeutic purposes. In one aspect, antisense to the polynucleotide encoding PRMP may be used in situations in which it would be desirable to block the transcription of the mRNA. In particular, cells may be transformed with sequences complementary to polynucleotides encoding PRMP. Thus, antisense molecules may be used to modulate PRMP activity, or to achieve regulation of gene function. Such technology is now well known in the art, and sense or antisense oligomers, or larger fragments, can be designed from various locations along the coding or control regions of sequences encoding PRMP.

Expression vectors derived from retrovirus, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense molecules complementary to the polynucleotides of the gene encoding PRMP. These techniques are described both in Sambrook et al. (supra) and in Ausubel et al. (supra).

Genes encoding PRMP can be turned off by transforming a cell or tissue with expression vectors which express high levels of a polynucleotide or fragment thereof which encodes PRMP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding PRMP, i.e., the promoters, enhancers, and introns. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding PRMP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding PRMP. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any subject in need of such therapy, including, for example, manunals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of PRMP, antibodies to PRMP, mimetics, agonists, antagonists, or inhibitors of PRMP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of PRMP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example PRMP or fragments thereof, antibodies of PRMP, agonists, antagonists or inhibitors of PRMP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind PRMP may be used for the diagnosis of conditions or diseases characterized by expression of PRMP, or in assays to monitor patients being treated with PRMP, agonists, antagonists or inhibitors. The antibodies useful for diagnostic purposes may be prepared in the same manner as those described above for therapeutics. Diagnostic assays for PRMP include methods which utilize the antibody and a label to detect PRMP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring PRMP are known in the art and provide a basis for diagnosing altered or abnormal levels of PRMP expression. Normal or standard values for PRMP expression are established by combining body fluids or cell extracts taken from normal mammalian subjects, preferably human, with antibody to PRMP under conditions suitable for complex formation The amount of standard complex formation may be quantified by various methods, preferably by photometric, means. Quantities of PRMP expressed in subject samples, control and disease from biopsied tissues are compared with the standard values. Deviation between standard and subject values establishes the parameters for diagnosing disease.

In another embodiment of the invention, the polynucleotides encoding PRMP may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of PRMP may be correlated with disease. The diagnostic assay may be used to distinguish between absence, presence, and excess expression of PRMP, and to monitor regulation of PRMP levels during therapeutic intervention.

In one aspect, hybridization with PCR probes which are capable of detecting polynucleotide sequences-including genomic sequences, encoding PRMP or closely related molecules, may be used to identify nucleic acid sequences which encode PRMP. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding PRMP, alleles, or related sequences.

Probes may also be used for the detection of related sequences, and should preferably contain at least 50% of the nucleotides from any of the PRMP encoding sequences. The hybridization probes of the subject invention may be DNA or RNA and derived from the nucleotide sequence of SEQ ID NO:2 or from genomic sequence including promoter, enhancer elements, and introns of the naturally occurring PRMP.

Means for producing specific hybridization probes for DNAs encoding PRMP include the cloning of nucleic acid sequences encoding PRMP or PRMP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding PRMP may be used for the diagnosis of disorders which are associated with expression of PRMP. Examples of such disorders include inflammatory and allergic conditions such as rheumatoid and osteoarthritis, asthma, allergic rhinitis, atopic dermatitis; autoimmune conditions such as Sjögren's syndrome, scleroderma, hyperthyroidism (Grave's disease), systemic lupus, myasthenia gravis, autoimmune thyroiditis, diabetes mellitus, pancreatitis, ulcerative colitis, Crohn's disease, atrophic gastritis, and graft-vs-host disease; disorders relating to abnormal cellular differentiation, proliferation, or degeneration, including arteriosclerosis, atherosclerosis, hyperaldosteronism, hypocortisolism (Addison's disease), hypothyroidism, colorectal polyps, gastric and duodenal ulcers, cancers of hematopoietic cells and lymphoid tissues including leukemias, lymphomas (including Hodgkin's disease), lymphosarcomas and myelomas, and carcinomas of glands, tissues, and organs involved in secretion or absorption, including prostate, pancreas, lung, tongue, brain, breast, and bladder, adrenal gland, thyroid, liver, uterus, kidney, testes, and organs of the gastrointestinal tract including small intestine, colon, rectum, and stomach. The polynucleotide sequences encoding PRMP may be used in Southern or northern analysis, dot blot, or other membrane-based technologies; in PCR technologies; or in dip stick, pin, ELISA or chip assays utilizing fluids or tissues from patient biopsies to detect altered PRMP expression. Such qualitative or quantitative methods are well known in the art.

In a particular aspect, the nucleotide sequences encoding PRMP may be useful in assays that detect activation or induction of various cancers, particularly those mentioned above. The nucleotide sequences encoding PRMP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding PRMP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of PRMP, a normal or standard profile for expression is established. This may be accomplished by combining body fluids or cell extracts taken from normal subjects, either animal or human, with a sequence, or a fragment thereof, which encodes PRMP, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding PRMP may involve the use of PCR. Such oligomers may be chemically synthesized, generated enzymatically, or produced from a recombinant source. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of PRMP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 212:229–236). The speed of quantitation of multiple samples may be accelerated by running the assay in an ELISA format where the oligomer of interest is presented in various dilutions and a spectrophotometric or calorimetric response gives rapid quantitation.

In another embodiment of the invention, the nucleic acid sequences which encode PRMP may also be used to generate hybridization probes which are useful for mapping the naturally occurring genomic sequence. The sequences may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981f). Correlation between the location of the gene encoding PRMP on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, PRMP, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between PRMP and the agent being tested, may be measured.

Another technique for drug screening which may be used provides for high throughput screening of compounds having suitable binding affinity to the protein of interest as described in published PCT application WO84/03564. In this method, as applied to PRMP, large numbers of different small test compounds are synthesized on a solid substrate, such as plastic pins or some other surface. The test compounds are reacted with PRMP, or fragments thereof, and washed. Bound PRMP is then detected by methods well known in the art. Purified PRMP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding PRMP specifically compete with a test compound for binding PRMP. In this manner, the antibodies can be used to detect the presence of any peptide which shares one or more antigenic determinants with PRMP.

In additional embodiments, the nucleotide sequences which encode PRMP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I THP1PLB02 cDNA Library Construction

THP-1 is a human leukemic cell line derived from the blood of a 1-year-old boy with acute monocytic leukemia. Cells used for the PMA+LPS library (THP1PLB02) were cultured for 48 hr with 100 nm PMA in DMSO and for 4 hr with 1 µg/ml LPS. The PMA+LPS-stimulated cells represent activated macrophages. The cDNA library was custom constructed by Stratagene essentially as described below.

Stratagene prepared the cDNA library using oligo d(T) priming. Synthetic adapter oligonucleotides were ligated onto the cDNA molecules enabling them to be inserted into the Uni-ZAP™ vector system (Stratagene). The PBLUESCRIPT phagemid (Stratagene) was excised and transfected into the XLI-BLUEX *E. coli* host strain (Stratagene).

II Isolation and Sequencing of cDNA Clones

The phagemid forms of individual cDNA clones were obtained by the in vivo excision process, in which the host bacterial strain was co-infected with both the library phage and an f1 helper phage. Enzymes derived from both the library-containing phage and the helper phage nicked the DNA, initiated new DNA synthesis from defined sequences on the target DNA, and created a smaller, single stranded circular phagemid DNA molecule that included all DNA sequences of the PBLUESCRIPT phagemid and the cDNA insert. The phagemid DNA was released from the cells, purified, and used to reinfect fresh host cells (SOLR, Stratagene) where double-stranded phagemid DNA was produced. Because the phagemid carries the gene for β-lactamase, the newly transformed bacteria were selected on medium containing ampicillin.

Phagemid DNA was released from cells and purified using a MINIPREP Kit (Cat. No. 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Cat. No. 22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60 µl of lysis buffer; 3) a centrifugation step employing the Beckman GS-6R at 2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying phagemid DNA include the use of a MAGIC MINIPREPS DNA Purification System (Cat. No. A7100, Promega) or QIAwell™-8 Plasmid, QIAwell PLUS DNA and QIAwell ULTRA DNA Purification Systems (Qiagen, Inc.).

The cDNAs were sequenced by the method of Sanger F. and A. R. Coulson (1975; J. Mol. Biol. 94:441f), using a Catalyst 800 (Perkin Elmer) or Hamilton Micro Lab 2200 (Hamilton, Reno Nev.) in combination with four Peltier Thermal Cyclers (PTC200 from M J Research, Watertown Mass.) and Applied Biosystems 377 or 373 DNA Sequencing Systems (Perkin Elmer) and reading frame was determined.

III Homology Searching of cDNA Clones and Their Deduced Proteins

Each cDNA was compared to sequences in the GenBank and EMBL databases using two homology search algorithms. The first algorithm was originally developed by Lipman D. J. and Pearson W. R. (1985; Science 227:1435). In this algorithm, the homologous regions are searched in a two-step manner. In the first step, highly homologous regions are determined by calculating a matching score using a homology score table. In this step, the parameter "Ktup" is used to establish a shifting, minimum window size for comparing two sequences. Ktup also sets the number of bases that must match to extract the highest homologous region among the sequences. In this step, no insertions or deletions are applied, and the homology is displayed as an initial (INIT) value.

In the second step, the homologous regions are aligned to obtain the highest matching score by inserting a gap when it is needed to accommodate a probable deletion. The matching score obtained in the first step is recalculated using the homology score table and the insertion score table to produce an optimized value.

DNA homologies between two sequences may also be examined graphically using the Harr method of constructing dot matrix homology plots (Needleman, S. B. and Wunsch, C. O. (1970) J. Mol. Biol. 48:443). This method produces a two-dimensional plot which can be useful in distinguishing between regions of homology and regions of repetition.

The second algorithm was developed by Applied Biosystems and incorporated into the INHERIT™ 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul, S. F. et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis, a laboratory technique used to detect the presence of a transcript of a gene, and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding PRMP occurs. Abundance and percent abundance are also reported. Abundance directly reflects the number of times a particular transcript is represented in a cDNA library, and percent abundance is abundance divided by the total number of sequences examined in the cDNA library.

V Extension of PRMP-Encoding Polynucleotides to Full Length or to Recover Regulatory Sequences Full length PRMP-encoding nucleic acid sequence (SEQ ID NO:2) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M. J. Research, Watertown, Mass.) and the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as QIAQUICK (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook et al., supra). After incubation for one hour at 37° C., the whole transformation mixture is plated on Luria Bertani (LB)-agar (Sambrook et al., supra) containing 2× Carb. The following day, several colonies are randomly picked from each plate and cultured in 150 µl of liquid LB/2× Carb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3×) containing 4 units of rTth DNA polymerase, a vector primer, and one or both of the gene specific primers used for the extension reaction are added to each well. Amplification is performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 µCi of [$\gamma$-$^{32}$P] adenosine triphosphate (Amersham) and T4 polynucleotide kinase (DuPont NEN®, Boston, Mass.). The labeled oligonucleotides are substantially purified with a SEPHADEX G-25 superfine resin column (Pharmacia & Upjohn). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots, or after the blots are exposed to Phosphoimager cassette (Molecular Dynamics, Sunnyvale, Calif.), hybridization patterns are compared visually.

VII Antisense Molecules

Antisense molecules to the PRMP-encoding sequence, or any part thereof, is used to inhibit in vivo or in vitro expression of naturally occurring PRMP. Although use of antisense oligonucleotides, comprising about 20 base-pairs, is specifically described, essentially the same procedure is used with larger cDNA fragments. An oligonucleotide based on the coding sequences of PRMP, as shown in FIGS. 1A, 1B, 1C, and 1D, is used to inhibit expression of naturally occurring PRMP. The complementary oligonucleotide is designed from the most unique 5' sequence as shown in FIGS. 1A, 1B, 1C, and 1D and used either to inhibit transcription by preventing promoter binding to the upstream nontranslated sequence or translation of an PRMP-encoding transcript by preventing the ribosome from binding. Using an appropriate portion of the signal and 5' sequence of SEQ ID NO:2, an effective antisense oligonucleotide includes any 15–20 nucleotides spanning the region which translates into the signal or 5' coding sequence of the polypeptide as shown in FIGS. 1A, 1B, 1C, and 1D.

VIII Expression of PRMP

Expression of PRMP is accomplished by subcloning the cDNAs into appropriate vectors and transforming the vectors into host cells. In this case, the cloning vector, pSport, previously used for the generation of the cDNA library is used to express PRMP in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of PRMP into the bacterial growth media which can be used directly in the following assay for activity.

IX Demonstration of PRMP Activity

To assay the ability of PRMP to bind to SH3 domains in vitro, a batch adsorption method is used. DNA encoding the SH3 domain of Src kinase (or other SH3 domain-containing protein) is cloned into a pGEX vector (Promega) and expressed in *E. coli* as a glutathione-S-transferase (GST) fusion protein. The SH3 domain-GST fusion protein is affixed to glutathione-SEPHAROSE beads (Pharmacia & Upjohn) to form an SH3 domain affinity matrix (Yang et. al, supra). PRMP is incubated with the affinity matrix with gentle rocking for 1 hour at 4° C. The matrix is then washed three times with 20 mM tris-Cl pH 8.3, 150 mM NaCl, 0.5% Nonidet P-40. Bound proteins are eluted by boiling in SDS sample buffer for 5 min and are fractionated on 7.5% or 10% SDS-PAGE (Sambrook, supra). PRMP is identified by immunoblotting with PRMP specific antibodies.

X Production of PRMP Specific Antibodies

PRMP that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431 A using finoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring PRMP Using Specific Antibodies

Naturally occurring or recombinant PRMP is substantially purified by immunoaffinity chromatography using antibodies specific for PRMP. An immunoaffinity column is constructed by covalently coupling PRMP antibody to an activated chromatographic resin, such as CnBr-activated SEPHAROSE (Pharmacia & Upjohn). After the coupling, the resin is blocked and washed according to the manufacturer's instructions.

Media containing PRMP is passed over the immunoaffinity column, and the column is washed under conditions that allow the preferential absorbance of PRMP (e.g., high ionic strength buffers in the presence of detergent). The column is eluted under conditions that disrupt antibody/PRMP binding (eg, a buffer of pH 2–3 or a high concentration of a chaotrope, such as urea or thiocyanate ion), and PRMP is collected.

XII Identification of Molecules Which Interact with PRMP

PRMP or biologically active fragments thereof are labeled with $^{125}$I Bolton-Hunter reagent (Bolton et al. (1973) Biochem. J. 133:529). Candidate molecules previously arrayed in the wells of a multi-well plate are incubated with the labeled PRMP, washed and any wells with labeled PRMP complex are assayed. Data obtained using different concentrations of PRMP are used to calculate values for the number, affinity, and association of PRMP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 311 amino acids
        ( B ) TYPE: amino acid
        ( C ) STRANDEDNESS: single
        ( D ) TOPOLOGY: linear ( v i i ) IMMEDIATE SOURCE:

(A) LIBRARY: Consensus
(B) CLONE: Consensus (xi) SEQUENCE DESCRIPTION: SEQ ID NO:1:

| Met | Ser | Asn | Pro | Ser | Ala | Pro | Pro | Tyr | Glu | Asp | Arg | Asn | Pro | Leu |
| 1 | | | | 5 | | | | | 10 | | | | | 15 |

| Tyr | Pro | Gly | Pro | Pro | Pro | Gly | Gly | Tyr | Gly | Gln | Pro | Ser | Val | Leu |
| | | | 20 | | | | 25 | | | | | 30 | | |

| Pro | Gly | Gly | Tyr | Pro | Ala | Tyr | Pro | Gly | Tyr | Pro | Gln | Pro | Gly | Tyr | Gly |
| | | 35 | | | | 40 | | | | | 45 | | | | |

| His | Pro | Ala | Gly | Tyr | Pro | Gln | Pro | Met | Pro | Pro | Thr | His | Pro | Met | Pro |
| | 50 | | | | | 55 | | | | | 60 | | | | |

| Met | Asn | Tyr | Gly | Pro | Gly | His | Gly | Tyr | Asp | Gly | Glu | Glu | Arg | Ala | Val |
| 65 | | | | | 70 | | | | | 75 | | | | | 80 |

| Ser | Asp | Ser | Phe | Gly | Pro | Gly | Glu | Trp | Asp | Asp | Arg | Lys | Val | Arg | His |
| | | | | 85 | | | | | 90 | | | | | 95 | |

| Thr | Phe | Ile | Arg | Lys | Val | Tyr | Ser | Ile | Ile | Ser | Val | Gln | Leu | Leu | Ile |
| | | | 100 | | | | | 105 | | | | | 110 | | |

| Thr | Val | Ala | Ile | Ile | Ala | Ile | Phe | Thr | Phe | Val | Glu | Pro | Val | Ser | Ala |
| | | | 115 | | | | 120 | | | | | 125 | | | |

| Phe | Val | Arg | Arg | Asn | Val | Ala | Val | Tyr | Tyr | Val | Ser | Tyr | Ala | Val | Phe |
| | 130 | | | | | 135 | | | | | 140 | | | | |

| Val | Val | Thr | Tyr | Leu | Ile | Leu | Ala | Cys | Cys | Gly | Pro | Arg | Arg | Arg |
| 145 | | | | | 150 | | | | | 155 | | | | 160 |

| Phe | Pro | Trp | Asn | Ile | Ile | Leu | Leu | Thr | Leu | Phe | Thr | Phe | Ala | Met | Gly |
| | | | | 165 | | | | | 170 | | | | | 175 | |

| Phe | Met | Thr | Gly | Thr | Ile | Ser | Ser | Met | Tyr | Gln | Thr | Lys | Ala | Val | Ile |
| | | | 180 | | | | | 185 | | | | | 190 | | |

| Ile | Ala | Met | Ile | Ile | Thr | Ala | Val | Val | Ser | Ile | Ser | Val | Thr | Ile | Phe |
| | | 195 | | | | | 200 | | | | | 205 | | | |

| Cys | Phe | Gln | Thr | Lys | Val | Asp | Phe | Thr | Ser | Cys | Thr | Gly | Leu | Phe | Cys |
| | 210 | | | | | 215 | | | | | 220 | | | | |

| Val | Leu | Gly | Ile | Val | Leu | Leu | Val | Thr | Gly | Ile | Val | Thr | Ser | Ile | Val |
| 225 | | | | | 230 | | | | | 235 | | | | | 240 |

| Leu | Tyr | Phe | Gln | Tyr | Val | Tyr | Trp | Leu | His | Met | Leu | Tyr | Ala | Ala | Leu |
| | | | | 245 | | | | | 250 | | | | | 255 | |

| Gly | Ala | Ile | Cys | Phe | Thr | Leu | Phe | Leu | Ala | Tyr | Asp | Thr | Gln | Leu | Val |
| | | | 260 | | | | | 265 | | | | | 270 | | |

| Leu | Gly | Asn | Arg | Lys | His | Thr | Ile | Ser | Pro | Glu | Asp | Tyr | Ile | Thr | Gly |
| | | 275 | | | | | 280 | | | | | 285 | | | |

| Ala | Leu | Gln | Ile | Tyr | Thr | Asp | Ile | Ile | Tyr | Ile | Phe | Thr | Phe | Val | Leu |
| | 290 | | | | | 295 | | | | | 300 | | | | |

| Gln | Leu | Met | Gly | Asp | Arg | Asn |
| 305 | | | | | 310 | |

(2) INFORMATION FOR SEQ ID NO:2:

(i) SEQUENCE CHARACTERISTICS:
(A) LENGTH: 2437 base pairs
(B) TYPE: nucleic acid
(C) STRANDEDNESS: single
(D) TOPOLOGY: linear (vii) IMMEDIATE SOURCE:
(A) LIBRARY: Consensus
(B) CLONE: Consensus (xi) SEQUENCE DESCRIPTION: SEQ ID NO:2:

```
ATGCCAGCCC CAAACCTCAT CCCTAGTGGA GGCCTTGCTG ATGTGGAAGT GGCCAGGGCC        60

CTCATGGTAG GCTGGGCAGA AGCCCAAGAA CAGGCTCTAA AGCTGCTAAA CCCGGCAGTC       120

CTGGTCCCCG GAGGCTCTTG CCAGTCTGAC AGTGTTCTTG GCACTGCTCA AAGGTCCCAG       180

CAGCTGGGGT TCCCCGTCAG CCCGTGAGCG GCCATGTCCA ACCCCAGCGC CCCACCACCA       240

TATGAAGACC GCAACCCCCT GTACCCAGGC CCTCCGCCCC TGGGGGCTA TGGGCAGCCA        300

TCTGTCCTGC CAGGAGGGTA TCCTGCCTAC CCTGGCTACC CGCAGCCTGG CTACGGTCAC       360

CCTGCTGGCT ACCCACAGCC CATGCCCCCC ACCCACCCGA TGCCCATGAA CTACGGCCCA       420

GGCCATGGCT ATGATGGGGA GGAGAGAGCG GTGAGTGATA GCTTCGGGCC TGGAGAGTGG       480

GATGACCGGA AAGTGCGACA CACTTTTATC CGAAAGGTTT ACTCCATCAT CTCCGTGCAG       540

CTGCTCATCA CTGTGGCCAT CATTGCTATC TTCACCTTTG TGGAACCTGT CAGCGCCTTT       600

GTGAGGAGAA ATGTGGCTGT CTACTACGTG TCCTATGCTG TCTTCGTTGT CACCTACCTG       660

ATCCTTGCCT GCTGCCAGGG ACCCAGACGC CGTTTCCCAT GGAACATCAT TCTGCTGACC       720

CTTTTTACTT TTGCCATGGG CTTCATGACG GGCACCATTT CCAGTATGTA CCAAACCAAA       780

GCCGTCATCA TTGCAATGAT CATCACTGCG GTGGTATCCA TTTCAGTCAC CATCTTCTGC       840

TTTCAGACCA AGGTGGACTT CACCTCGTGC ACAGGCCTCT TCTGTGTCCT GGGAATTGTG       900

CTCCTGGTGA CTGGGATTGT CACTAGCATT GTGCTCTACT TCCAATACGT TTACTGGCTC       960

CACATGCTCT ATGCTGCTCT GGGGGCCATT TGTTTCACCC TGTTCCTGGC TTACGACACA      1020

CAGCTGGTCC TGGGGAACCG GAAGCACACC ATCAGCCCCG AGGACTACAT CACTGGCGCC      1080

CTGCAGATTT ACACAGACAT CATCTACATC TTCACCTTTG TGCTGCAGCT GATGGGGGAT      1140

CGCAATTAAG GAGCAAGCCC CCATTTTCAC CCGATCCTGG GCTCTCCCTT CCAAGCTAGA      1200

GGGCTGGGCC CTATGACTGT GGTCTGGGCT TTAGGCCCCT TTCCTTCCCC TTGAGTAACA      1260

TGCCCAGTTT CCTTTCTGTC CTGGAGACAG GTGGCCTCTC TGGCTATGGA TGTGTGGGTA      1320

CTTGGTGGGG ACGGAGGAGC TAGGGACTAA CTGTTGCTCT TGGTGGGCTT GGCAGGGACT      1380

AGGCTGAAGA TGTGTCTTCT CCCCGCCACC TACTGTATGA CACCACATTC TTCCTAACAG      1440

CTGGGGTTGT GAGGAATATG AAAAGAGCCT ATTCGATAGC TAGAAGGGAA TATGAAAGGT      1500

AGAAGTGACT TCAAGGTCAC GAGGTTCCCC TCCCACCTCT GTCACAGGCT TCTTGACTAC      1560

GTAGTTGGAG CTATTTCTTC CCCCAGCAAA GCCAGAGAGC TTTGTCCCCG GCCTCCTGGA      1620

CACATAGGCC ATTATCCTGT ATTCCTTTGG CTTGGCATCT TTTAGCTCAG GAAGGTAGAA      1680

GAGATCTGTG CCCATGGGTC TCCTTGCTTC AATCCCTTCT TGTTTCAGTG ACATATGTAT      1740

TGTTTATCTG GGTTAGGGAT GGGGGACAGA TAATAGAACG AGCAAAGTAA CCTATACAGG      1800

CCAGCATGGA ACAGCATCTC CCCTGGGCTT GCTCCTGGCT TGTGACGCTA TAAGACAGAG      1860

CAGGCCACAT GTGGCCATCT GCTCCCCATT CTTGAAAGCT GCTGGGGCCT CCTTGCAGGC      1920

TTCTGGATCT CTGGTCAGAG TGAACTCTTG CTTCCTGTAT TCAGGCAGCT CAGAGCAGAA      1980

AGTAAGGGGC AGAGTCATAC GTGTGGCCAG GAAGTAGCCA GGGTGAAGAG AGACTCGGTG      2040

CGGGCAGGGA GAATGCCTGG GGGTCCCTCA CCTGGCTAGG GAGATACCGA AGCCTACTGT      2100

GGTACTGAAG ACTTCTGGGT TCTTTCCTTC TGCTAACCCA GGGAGGGTCC TAAGAGGAAG      2160

GTGACTTCTC TCTGTTTGTC TTAAGTTGCA CTGGGGATT TCTGACTTGA GGCCCATCTC       2220

TCCAGCCAGC CACTGCCTTC TTTGTAATAT TAAGTGCCTT GAGCTGGAAT GGGGAAGGGG      2280

GACAAGGGTC AGTCTGTCGG GTGGGGGCAG AAATCAAATC AGCCCAAGGA TATAGTTAGG      2340

ATTAATTACT TAATAGAGAA ATCCTAACTA TATCACACAA AGGGATACAA CTATAAATGT      2400
```

AATAAAATTT ATGTCTAGAA GTTAAAAAAA AAAAAA 2437

( 2 ) INFORMATION FOR SEQ ID NO:3:

( i ) SEQUENCE CHARACTERISTICS:
        ( A ) LENGTH: 516 amino acids
        ( B ) TYPE: amino acid
        ( C ) STRANDEDNESS: single
        ( D ) TOPOLOGY: linear ( v i i ) IMMEDIATE SOURCE:
        ( A ) LIBRARY: GenBank
        ( B ) CLONE: 238267

( x i ) SEQUENCE DESCRIPTION: SEQ ID NO:3:

```
Met Lys Arg Val Ser Trp Ser Leu Gly Thr Ala Ile Leu Pro Gln Thr
  1               5                  10                  15

Leu Ala Ile Leu Trp Gly His Lys Pro Leu Cys Leu Pro Met Phe Ser
             20                  25                  30

Leu Pro Thr Leu Gly Pro His Thr His Arg Pro Leu Ser Ser Pro Leu
         35                  40                  45

Pro Met Val Asn Gln Gly Ile Pro Met Val Pro Val Pro Ile Thr Arg
     50                  55                  60

Trp Leu Pro Leu Lys Asp Leu Leu Lys Glu Ala Thr His Gln Gly His
 65                  70                  75                  80

Tyr Pro Gln Ser Pro Phe Pro Pro Asn Pro Tyr Gly Gln Pro Pro Pro
                 85                  90                  95

Phe Gln Asp Pro Gly Ser Pro Gln His Gly Asn Tyr Gln Glu Glu Gly
            100                 105                 110

Pro Pro Ser Tyr Tyr Asp Asn Gln Asp Phe Pro Ser Val Asn Trp Asp
            115                 120                 125

Lys Ser Ile Arg Gln Ala Phe Ile Arg Lys Val Phe Leu Val Leu Thr
        130                 135                 140

Leu Gln Leu Ser Val Thr Leu Ser Thr Val Ala Ile Phe Thr Phe Val
145                 150                 155                 160

Gly Glu Val Lys Gly Phe Val Arg Ala Asn Val Trp Thr Tyr Tyr Val
                165                 170                 175

Ser Tyr Ala Ile Phe Phe Ile Ser Leu Ile Val Leu Ser Cys Cys Gly
            180                 185                 190

Asp Phe Arg Lys Lys His Pro Trp Asn Leu Val Ala Leu Ser Ile Leu
        195                 200                 205

Thr Ile Ser Leu Ser Tyr Met Val Gly Met Ile Ala Ser Phe Tyr Asn
    210                 215                 220

Thr Glu Ala Val Ile Met Ala Val Gly Ile Thr Thr Ala Val Cys Phe
225                 230                 235                 240

Thr Val Val Ile Phe Ser Met Gln Thr Arg Tyr Asp Phe Thr Ser Cys
                245                 250                 255

Met Gly Val Leu Leu Val Ser Val Val Val Leu Phe Ile Phe Ala Ile
            260                 265                 270

Leu Cys Ile Phe Ile Arg Asn Arg Ile Leu Glu Ile Val Tyr Ala Ser
        275                 280                 285

Leu Gly Ala Leu Leu Phe Thr Cys Phe Leu Ala Val Asp Thr Gln Leu
    290                 295                 300

Leu Leu Gly Asn Lys Gln Leu Ser Leu Ser Pro Glu Glu Tyr Val Phe
305                 310                 315                 320

Ala Ala Leu Asn Leu Tyr Thr Asp Ile Ile Asn Ile Phe Leu Tyr Ile
                325                 330                 335
```

-continued

| | | | | | | | | | | | | | | | |
|---|---|---|---|---|---|---|---|---|---|---|---|---|---|---|---|
| Leu | Thr | Ile | Ile<br>340 | Gly | Arg | Ser | Gln | Gly<br>345 | Ile | Gly | Gln | Ala | Pro<br>350 | Ala | Gln |
| Val | Ala | Trp<br>355 | Trp | Ala | Gln | Thr | His<br>360 | Ala | Pro | Gly | Met | Thr<br>365 | Leu | Pro | Ser |
| Val | Leu<br>370 | Pro | Pro | Leu | Trp | Phe<br>375 | Pro | Ala | Met | Ala | Trp<br>380 | Ser | Arg | Gly | Ser |
| Pro<br>385 | Ser | Arg | Pro | Arg | Val<br>390 | Cys | Thr | Leu | Gln | Ile<br>395 | Leu | Asn | Val | Arg | Thr<br>400 |
| Leu | Ser | Ala | Thr | Ala<br>405 | Trp | Lys | Pro | Leu | Ser<br>410 | Leu | Leu | Pro | Leu | Pro<br>415 | Arg |
| Gly | Asp | Arg | Ala<br>420 | Ala | Phe | Leu | Cys | His<br>425 | Leu | Leu | Ser | Thr | His<br>430 | Cys | Cys |
| Met | Ser | Pro<br>435 | Val | Cys | Gln | Pro | Ile<br>440 | Pro | Gly | Ser | Gly | Ile<br>445 | Asn | Thr | Arg |
| Ser | Gln<br>450 | Gly | Arg | Arg | Ile | Ile<br>455 | Pro | Arg | Gly | Glu | Gly<br>460 | Ala | Arg | Leu | Pro |
| Ser<br>465 | Cys | Pro | Ser | Ser | Pro<br>470 | Gly | Ile | Glu | Ser | Pro<br>475 | Cys | Pro | Leu | Leu | Thr<br>480 |
| Leu | Pro | Ser | Glu | Gly<br>485 | Leu | Ala | Gly | Trp | Gly<br>490 | Leu | Val | Leu | Val | Leu<br>495 | Gly |
| Pro | Glu | Thr | Lys<br>500 | Arg | Gly | Trp | His | Val<br>505 | Ser | Gly | Glu | Arg | Leu<br>510 | Ser | Cys |
| Val | Leu | Pro<br>515 | Leu | | | | | | | | | | | | |

What is claimed is:

1. An isolated and purified polynucleotide sequence encoding a polypeptide comprising the amino acid sequence of SEQ ID NO:1.

2. An isolated and purified polynucleotide sequence which hybridizes under stringent wash conditions of 0.1× saline sodium citrate and 0.5% sodium dodecyl sulfate to the polynucleotide sequence of claim 1.

3. A hybridization probe comprising the polynucleotide sequence of claim 1.

4. An isolated and purified polynucleotide sequence comprising SEQ ID NO:2.

5. An isolated and purified polynucleotide sequence which is fully complementary to the polynucleotide sequence of claim 1.

6. A hybridization probe comprising the polynucleotide sequence of claim 5.

7. An expression vector containing the polynucleotide sequence of claim 1.

8. A host cell containing the expression vector of claim 7.

9. A method for producing a polypeptide comprising the amino acid sequence of SEQ ID NO:1, the method comprising the steps of:

a) culturing the host cell of claim 8 under conditions suitable for the expression of the polypeptide; and b) recovering the polypeptide from the host cell culture.

* * * * *